United States Patent
Findikoglu et al.

(10) Patent No.: US 10,473,625 B2
(45) Date of Patent: Nov. 12, 2019

(54) DETECTION AND MONITORING OF CHANGES IN METALLIC STRUCTURES USING MULTIMODE ACOUSTIC SIGNALS

(71) Applicants: Triad National Security, LLC, Los Alamos, NM (US); Chevron U.S.A. Inc., San Ramon, CA (US)

(72) Inventors: Alp T. Findikoglu, Santa Fe, NM (US); Dipen N. Sinha, Los Alamos, NM (US); Daniel R. Chapman, Oakland, CA (US)

(73) Assignees: Chevron U.S.A. Inc., San Ramon, CA (US); Triad National Security, LLC, Los Alamos, CA (US)

( * ) Notice: Subject to any disclaimer, the term of this patent is extended or adjusted under 35 U.S.C. 154(b) by 48 days.

(21) Appl. No.: 15/751,429

(22) PCT Filed: Aug. 12, 2016

(86) PCT No.: PCT/US2016/046919
§ 371 (c)(1),
(2) Date: Feb. 8, 2018

(87) PCT Pub. No.: WO2017/099852
PCT Pub. Date: Jun. 15, 2017

(65) Prior Publication Data
US 2018/0231501 A1  Aug. 16, 2018

Related U.S. Application Data

(60) Provisional application No. 62/204,222, filed on Aug. 12, 2015.

(51) Int. Cl.
*G01N 29/04* (2006.01)
*G01F 1/66* (2006.01)
(Continued)

(52) U.S. Cl.
CPC ............ *G01N 29/043* (2013.01); *G01F 1/66* (2013.01); *G01F 1/708* (2013.01); *G01F 1/74* (2013.01);
(Continued)

(58) Field of Classification Search
CPC ............... G01N 29/043; G01N 29/348; G01N 2291/015; G01N 2291/0256; G01N 2291/0258
See application file for complete search history.

(56) References Cited

U.S. PATENT DOCUMENTS 4,623,468 A   11/1986 Lepain
4,890,055 A   12/1989 Van Broekhoven et al.
(Continued)

FOREIGN PATENT DOCUMENTS

WO   2017099852   6/2017

OTHER PUBLICATIONS

PCT International Search Report and Written Opinion, dated Jan. 6, 2017, issued in International Application No. PCT/US2016/046919, filed on Aug. 12, 17 pages.

*Primary Examiner* — Michael J Dalbo
(74) *Attorney, Agent, or Firm* — Samuel M. Freund; Cochran Freund & Young LLC

(57) ABSTRACT

Methods for detecting and monitoring changes in mechanical structures and in walls of pipes, vessels and storage tanks, using multimode acoustic signal propagation and detection, are described. Acoustic signals having chosen amplitude-time-frequency characteristics excite multiple modes in the structure under investigation, are generated and received at a small number of accessible locations, such as the ends of pipes and the tops and bottoms of vessels and storage tanks, with the inspection region between transmit and receive transducers. Small mechanical changes lead to (Continued)

acoustic scattering and attenuation among the various modes, which are detectable as changes in received signal intensity. Such changes may include material loss, material conversion and material addition. Once the structure is characterized in a known condition, the present method may be used to monitor the structure at a later time to determine whether changes have taken place. Methods for effective temperature compensation are also described. In addition, various pipe geometries and complex pipe geometries involving elbows, flanges, and the like can be monitored.

38 Claims, 13 Drawing Sheets

(51) Int. Cl.
    *G01F 1/708*     (2006.01)
    *G01F 1/74*     (2006.01)
    *G01N 29/32*     (2006.01)
    *G01N 29/34*     (2006.01)
    *G01N 29/44*     (2006.01)
    *G01N 29/46*     (2006.01)
    *G01N 29/07*     (2006.01)

(52) U.S. Cl.
    CPC ........... *G01N 29/07* (2013.01); *G01N 29/326* (2013.01); *G01N 29/343* (2013.01); *G01N 29/348* (2013.01); *G01N 29/449* (2013.01); *G01N 29/4409* (2013.01); *G01N 29/4463* (2013.01); *G01N 29/4472* (2013.01); *G01N 29/46* (2013.01); *G01N 2291/011* (2013.01); *G01N 2291/0258* (2013.01); *G01N 2291/2634* (2013.01)

(56) References Cited

U.S. PATENT DOCUMENTS

| | | |
|---|---|---|
| 5,526,689 A | 6/1996 | Coulter |
| 5,987,990 A | 11/1999 | Worthington |
| 7,307,914 B1 | 12/2007 | Carter |
| 8,225,665 B2 | 7/2012 | Geir |
| 9,632,062 B2 | 4/2017 | Tanaka |
| 2007/0017800 A1* | 1/2007 | Cetinkaya ............... C23C 14/34 204/192.1 |
| 2007/0072137 A1* | 3/2007 | Peluso ................... G01N 17/00 431/13 |
| 2009/0150094 A1* | 6/2009 | Van Velsor ............ G01N 29/07 702/39 |
| 2010/0079258 A1 | 4/2010 | Ihn |
| 2010/0278008 A1 | 11/2010 | Ammar |
| 2011/0301882 A1 | 12/2011 | Andersen |
| 2012/0055253 A1 | 3/2012 | Sinha |
| 2012/0055264 A1 | 3/2012 | Sinha |
| 2015/0053009 A1* | 2/2015 | Yan ........................ G01N 29/07 73/598 |
| 2015/0212048 A1 | 7/2015 | Ganesan |
| 2018/0292356 A1 | 10/2018 | Findikoglu |

* cited by examiner

DETECTION AND MONITORING OF CHANGES IN METALLIC STRUCTURES USING MULTIMODE ACOUSTIC SIGNALS

CROSS-REFERENCE TO RELATED APPLICATIONS

The present application claims the benefit of PCT Patent Application Number PCT/US2016/046919 for "Detection And Monitoring Of Changes In Metallic Structures Using Multimode Acoustic Signals" which was filed on Aug. 12, 2016, and U.S. Provisional Patent Application No. 62/204,222 for "Detection And Monitoring Of Changes In Metallic Structures Using Multimode Acoustic Signals" which was filed on Aug. 12, 2015, the entire contents of which these applications are hereby specifically incorporated by reference herein for all that they disclose and teach.

STATEMENT REGARDING FEDERAL RIGHTS

This invention was made with government support under Contract No. DE AC52-06NA25396 awarded by the U.S. Department of Energy. The government has certain rights in the invention.

FIELD OF THE INVENTION

The present invention relates generally to the detection of and monitoring of changes in mechanical structures, pipes, vessels, and storage containers and, more particularly, to the use of multimode acoustic signal propagation and signal detection for detecting and monitoring changes in mechanical structures, and in walls of pipes, vessels, and storage containers.

BACKGROUND

Detection of and monitoring of material loss due to pitting, cracking and fractures, material conversion from corrosion and/or erosion, and material addition from material migration and accumulation, and material adsorption, as examples, in mechanical structures, and walls of pipes, vessels, and storage tanks in hard-to-access environments, such as under insulation or under paint, are important in many industries that involve liquid or gas storage and flow.

Currently, the detection of corrosion under insulation is done most effectively by visual inspection by removing the insulation, which is time consuming and costly. Other methods of detection include radiography, eddy current techniques, x-ray, remote TV monitoring, electromagnetic devices, local acoustic interrogation, and long-range acoustic interrogation using an array of acoustic transducers. These methods are not widely used because the information provided has too limited a range to be of practical value, or the apparatus involved is too cumbersome or expensive to implement.

SUMMARY OF THE INVENTION

Embodiments of the present invention include, but are not limited to, overcoming the disadvantages and limitations of the prior art by providing a method for the detection of and monitoring of changes in mechanical structures, pipes, vessels, and storage containers over time, using temperature compensation when needed.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

To achieve the foregoing and other objects, and in accordance with the purposes of embodiments of the present invention, as embodied and broadly described herein, the method for detection and monitoring changes in an elongated metallic structure having a wall and an exterior surface, hereof includes: placing at least one acoustic transmitting transducer in vibrational communication with the exterior surface of the metallic structure; placing at least one receiving transducer in vibrational communication with the exterior surface of said metallic structure and spaced apart a chosen length from the at least one transmitting transducer; generating acoustic frequency chirp signals having a selected signal strength, spectral content, and duration; directing the chirp signals to the at least one transmitting transducer; producing a baseline signal by; receiving the vibrational signals generated in the wall of the metallic structure in response to the chirp signal by the receiving transducer; averaging a chosen number of received vibrational signals; and removing any DC component from the averaged received signals; producing a monitoring signal by: receiving the vibrational signals generated in the wall of the metallic structure in response to the chirp signal by the receiving transducer; averaging a chosen number of received vibrational signals; and removing any DC component from the averaged received signals; normalizing the monitoring signal to the baseline signal, whereby a maximum value of each of the baseline signal and the monitoring signal is equal to a selected value; performing short-time Fourier Transforms of the baseline and monitoring signals using chosen time and frequency window sizes, and time steps; taking the difference between the normalized monitoring signal and the normalized baseline signal, forming thereby a two-dimensional contour map; identifying at least one frequency-time mode pair in the contour map indicative of at least one scattering event, where one feature of the at least one frequency-time mode pair has a maximum positive value and the corresponding feature of the at least one frequency-time mode pair has a maximum negative value; and calculating the amplitude difference between maximum positive value and the maximum negative value.

In another aspect of embodiments of the present invention and in accordance with their objects and purposes, the method for detection and monitoring changes in an elongated metallic structure having a wall and an exterior surface, hereof includes: placing at least one acoustic transmitting transducer in vibrational communication with the exterior surface of the metallic structure; placing at least one receiving transducer in vibrational communication with the exterior surface of the metallic structure and spaced apart a chosen length from the at least one transmitting transducer; generating acoustic frequency chirp signals having a selected signal strength, spectral content, and duration; directing the chirp signals to the at least one transmitting transducer; producing a baseline signal by: receiving the vibrational signals generated in the wall of the metallic structure in response to the chirp signal by the receiving transducer; averaging a chosen number of received vibrational signals; and removing any DC component from the averaged received signals; producing a monitoring signal by: receiving the vibrational signals generated in the wall of the metallic structure in response to the chirp signal by the receiving transducer; averaging a chosen number of received vibrational signals; and removing any DC component from the averaged received signals; normalizing the monitoring signal to the baseline signal, whereby a maximum value of each of the baseline and the monitoring signals is equal to a selected value; taking the difference between the monitoring signal and the baseline signal, forming a difference signal; performing short-time Fourier transform of the difference signal using chosen time and frequency window sizes, and time steps, forming thereby a two-dimensional array in time and frequency; calculating the standard deviation of the short-time Fourier transform array along the time-axis for each frequency; and summing the standard deviations as a function of frequency.

In yet another aspect of embodiments of the present invention and in accordance with their objects and purposes the method for detection and monitoring changes in an elongated metallic structure having a wall and an exterior surface, hereof includes: placing at least one acoustic transmitting transducer in vibrational communication with the exterior surface of the metallic structure; placing at least one receiving transducer in vibrational communication with the exterior surface of the metallic structure and spaced apart a chosen length from said at least one transmitting transducer; generating acoustic frequency chirp signals having a selected signal strength, spectral content, and duration; directing the chirp signals to the at least one transmitting transducer; producing a baseline signal by: receiving the vibrational signals generated in the wall of the metallic structure in response to the chirp signal by the receiving transducer; averaging a chosen number of received vibrational signals; and removing any DC component from the averaged received signals; producing a monitoring signal by: receiving the vibrational signals generated in the wall of the metallic structure in response to the chirp signal by the receiving transducer; averaging a chosen number of received vibrational signals; and removing any DC component from the averaged received signals; normalizing the monitoring signal to the baseline signal, whereby a maximum value of each of the baseline signal and the monitoring signal is equal to a selected value; performing temperature compensation of the monitoring signal using the baseline signal as a comparison signal, thereby producing a temperature-compensated monitoring signal; performing short-time Fourier Transforms of the baseline and temperature-compensated monitoring signals using chosen time and frequency window sizes, and time steps; taking the difference between the normalized monitoring signal and the normalized baseline signal, forming thereby a two-dimensional contour map; identifying at least one frequency-time mode pair in the contour map indicative of at least one scattering event, where one feature of the at least one frequency-time mode pair has a maximum positive value and the corresponding feature of the at least one frequency-time mode pair has a maximum negative value; and calculating the amplitude difference between maximum positive value and the maximum negative value.

In still another aspect of embodiments of the present invention and in accordance with their objects and purposes the method for detection and monitoring changes in an elongated metallic structure having a wall and an exterior surface, hereof includes: placing at least one acoustic transmitting transducer in vibrational communication with the exterior surface of the metallic structure; placing at least one receiving transducer in vibrational communication with the exterior surface of the metallic structure and spaced apart a chosen length from the at least one transmitting transducer; generating acoustic frequency chirp signals having a selected signal strength, spectral content, and duration; directing the chirp signals to the at least one transmitting transducer; producing a baseline signal by: receiving the vibrational signals generated in the wall of the metallic structure in response to the chirp signal by the receiving transducer; averaging a chosen number of received vibrational signals; and removing any DC component from the averaged received signals; producing a monitoring signal by: receiving the vibrational signals generated in the wall of the metallic structure in response to the chirp signal by the receiving transducer; averaging a chosen number of received vibrational signals; and removing any DC component from the averaged received signals; normalizing the monitoring signal to the baseline signal, whereby a maximum value of each of the baseline and the monitoring signals is equal to a selected value; performing temperature compensation of the monitoring signal using the baseline signal as a comparison signal, thereby producing a temperature-compensated monitoring signal; taking the difference between the temperature-compensated monitoring signal and the baseline signal, forming a difference signal; performing short-time Fourier transform of the difference signal using chosen time and frequency window sizes, and time steps, forming thereby a two-dimensional array in time and frequency; calculating the standard deviation of the short-time Fourier transform array along the time-axis for each frequency; and summing the standard deviations as a function of frequency.

Benefits and advantages of embodiments of the present invention include, but are not limited to, providing a method for the detection of and the monitoring of changes, including material loss, material conversion and material addition, over time in mechanical structures, pipes, vessels, and storage containers. In addition, various pipe geometries and complex pipe geometries involving elbows, flanges, and the like can be monitored.

BRIEF DESCRIPTION OF THE DRAWINGS

The accompanying drawings, which are incorporated in and form a part of the specification, illustrate the embodiments of the present invention and, together with the description, serve to explain the principles of the invention. In the drawings:

FIG. 1A is a schematic representation of an embodiment of the basic apparatus suitable for practicing embodiments of the method of the present invention showing a linear pipe section, while

FIG. 11A is a graph of the signal difference amplitude as a function of time for both temperature compensated and non-temperature-compensated signals for a 25 ft. section of a 105-ft long pipe assembly, while

FIG. 12A is a graph of the signal difference amplitude as a function of time for both temperature compensated and non-temperature-compensated signals for a 50 ft. section of a 105-ft long pipe assembly, while

FIG. 13A is a graph of the signal difference amplitude as a function of time for both temperature compensated and non-temperature-compensated signals for a 100 ft. section of a 105-ft long pipe assembly, while

DETAILED DESCRIPTION

Figure 1A:
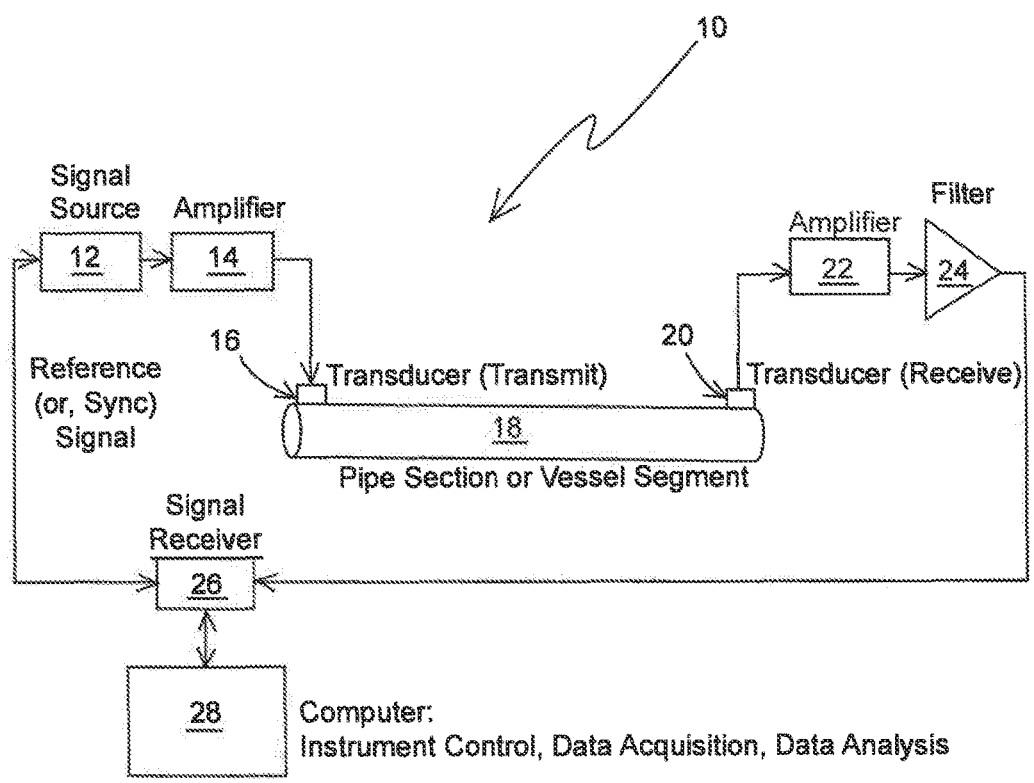

Briefly, embodiments of the present invention include methods for acoustic detection and large area monitoring of corrosion and/or erosion, and other defects of metallic structures, such as pipes, vessels, storage tanks, elbows, flanges, reducers, tees, and welds, as examples, in difficult-to-access environments, such as under insulation or under paint. In addition, various pipe geometries and complex pipe geometries involving elbows, flanges, and the like can be monitored.

The present method includes: (i) acoustic signal generation, transmission, and reception with amplitude, time and frequency characteristics that are optimized for the structure/pipe/vessel/tank, and anticipated defect(s); (ii) acoustic data acquisition and numerical analysis of acquired data; and (iii) mapping of amplitude, time and frequency acoustic data characteristics and analysis results into actionable information, for defect identification and defect quantification.

Detectable and identifiable changes in signal energy distribution among the allowed multiple acoustic modes result from the effect of mechanical changes or defects on the propagation of multi-mode acoustic signals through many pipes and vessels (or, systems), although the total energy of the acoustic signal is quasi-conserved. That is, defects principally lead to elastic scattering of acoustic waves from one mode to another, while the attenuation of total acoustic signal energy is generally small. Mechanical perturbations effective for generating acoustic scattering and attenuation include material loss (pitting, cracks, fractures, and erosion), material conversion (corrosion products), material addition (material migration and accumulation, and material adsorption, each of which having particular scattering/attenuation characteristics in amplitude, time, and frequency phase space.

In accordance with the teachings of embodiments of the present invention, acoustic signals are generated and received at a small number of accessible and convenient locations, such as the ends of pipes, or top and bottom sections of vessels, storage tanks, or elbows, flanges, reducers, tees, or welds, etc. Acoustic signals having amplitude, time and frequency characteristics effective for exciting multiple modes of interest in the pipe, vessel, tank, elbow, flange, reducer, tee, or weld, and such signals propagate in the inspection zone between transmit and receive transducers. Once the structure, pipe, vessel, tank, elbow, flange, reducer, tee, or weld, is characterized in a known or baseline state or condition, such as immediately after installation or after a detailed inspection, the present methods monitor small changes in the transmission characteristics of the acoustic signals in the inspection zone, and identifies and quantifies the defect formation continually or on-demand, for example, several times per day, once a week, or once a month, over many years by signal subtraction. The acoustic output may be accessed by embedded or mechanically-attached transducers, or by non-contact air coupling, as examples.

The acoustic data acquisition may be optimized for high signal-to-noise ratio in the system of interest. Signal analysis combines amplitude, time- and frequency-domain measurements of the signals using Fourier Transforms, Short-Time Fourier Transforms, Wavelet Transforms, Phase Delay Analysis, Hilbert Spectral Analysis, and Hilbert-Huang Transforms, as examples, with the identification and measurement of changes in such multi-dimensional data sets from those of the baseline condition.

The mapping of measured signal characteristics and analysis results for defect identification and quantification allows for interpretation of measured and analyzed data as actionable information.

The received acoustic data is in the form of a transmitted electrical signal amplitude as a function of time, and is precisely timed relative to repetitive input excitation in the form of a chirp signal, as an example (using a trigger signal from signal source to receiver instrument), so that one can use time-averaging (usually between 64 and 4096 times). Time-averaging improves signal-to-noise ratio (SNR) and makes the method relatively insensitive to other acoustic (noise) sources in the environment. Filtering the received signal in the frequency domain permits only the spectral components of interest to reach the receiver, thereby further improving SNR.

The time-averaged and filtered received signal is then transformed into a two-dimensional contour/surface map using a Short-Time-Fourier-Transform (STFT) algorithm with optimized parameters of window size, and step size, which may vary depending on the length of the pipe (vessel), and/or characteristics of the pipe or vessel. The STFT map displays the distribution of received signal strength as a function of time and frequency; that is, which frequency components of the transmitted signal arrived, when and with what strength. Joint spectral and time-delay information permits baseline characteristics of the pipe or vessel, as well as the effects of perturbations to the pipe or vessel on the acoustic signal transmission, to be characterized.

The baseline STFT map constitutes the reference level, against which perturbation effects, such as material addition and removal from the pipe wall, water accumulation on pipe walls, material contact with pipe walls, material transformation of pipe walls due to corrosion, strain in pipe walls due to sagging which might be caused by filling of the pipe with liquid, etc.

Detection sensitivity of embodiments of the present method is the minimum amount of perturbation that can be reproducibly measured; embodiments of the present method have measured perturbation effects due to both material addition and material removal from pipe or vessel walls at levels of <1% local volume change at pipe lengths of up to about 100 ft. Detection selectivity requires distinguishing among the direct causes of acoustic perturbation, such as water accumulation on pipe walls, clamping, sagging, material conversion or loss due to corrosion, material loss due to corrosion pitting, contact of pipe wall with a foreign solid object, etc. For example, water on pipe walls generates relatively uniform attenuation over a wide spectral range of signals, with minimal scattering, and it is therefore readily distinguishable from corrosion pitting and other defects on the pipe which predominantly lead to elastic scattering among specific acoustic modes propagating along the walls of pipes and vessels into other modes with specific time delays.

Paint on the walls (or, chips in the paint) of pipes or vessels have much smaller effect than corrosion and other defects. Insulation around the pipes and vessels also produces a weak effect on the acoustic wave transmission compared to corrosion or other defect formation on the pipes and vessels. Clamping a pipe leads to large scattering of acoustic signals and can overwhelm in magnitude scattering effects due to corrosion or other defects. However, the frequency distribution of scattering due to clamping is expected to be much broader than what one would expect from local corrosion scattering, and thus scattering signals can be distinguished. False signals from the effects of clamping may also be avoided by generating a new baseline when a clamp is added or removed from a pipe section.

A foreign solid material locally placed against a pipe is expected to produce acoustic signal scattering similar to those due to material addition to a pipe or vessel wall, and it is expected that it would be difficult to distinguish these effects. Sagging due to weight of a component over time is expected to lead to a spatially diffuse strain field in the pipe. Such a delocalized strain field could lead to weak scattering and attenuation of acoustic waves. However, both the magnitude and the spectral features of such scattering and attenuation should be discernible from scattering due to localized perturbations from corrosion or other defects. To date, perturbation sources have been individually characterized.

Detection robustness or reliability refers to the long-term viability of the present method, where a baseline can be used to monitor perturbation effects over long time periods, many years in certain applications. To achieve such robustness and reliability, effects of temperature are compensated for, and detrimental environmental noise is filtered. Temperature effects include: acoustic transducer response; coupling coefficient between the transducer and the interrogated medium, such as a pipe; acoustic signal propagation in the medium; and the transfer function of the electronics. The characteristics and relative importance of temperature effects due to each of these components will depend on the specifics of the overall system. However, if the temperature is recorded when initial measurements are made, and subsequent measurements are made within a few degrees Celsius of that temperature, such temperature effects may be too small to alter measurement results. However, if the temperature variation is more than a few degrees Celsius, it may be necessary to employ a method for temperature compensation. Similarly, environmental noise depends on the location where the system resides; thus, noise filtering may be tailored to the specifics of the environment.

As will be described below, use of a temperature compensation algorithm has been found to increase the signal-to-noise (S/N) ratio, thereby improving measurement sensitivity.

Embodiments of the present Normalized-Difference, Short-Time Fourier Transform (ND-STFT) method include detection of corrosion in pipes, vessels and structures using acoustic interrogation from a limited number and area of access locations (minimum of two, at two ends of a pipe for excitation and reception of transmitted acoustic signals, the section between the two transducers thereby being monitored). Typically, transmitting and receiving transducers are uniformly distributed over the surface of a pipe about 10 feet to approximately 100 feet apart, with the portion to be monitored therebetween. The pipe section may be straight, curved, flanged, or could have welded portions on it. Pipe sections may be between 10 ft and 100 ft in most cases, and the present method is similarly applicable to situations where cross-sectional dimensions of the pipe are much smaller than the length of the pipe. Large flanges, T-sections, or 4-way or 6-way crosses attached to a pipe may be monitored separately.

Reference will now be made in detail to the present embodiments of the invention, examples of which are illustrated in the accompanying drawings. In the FIGURES, similar structure will be identified using identical reference characters. It will be understood that the FIGURES are for the purpose of describing particular embodiments of the invention and are not intended to limit the invention thereto. Turning now to FIG. 1A, a schematic representation of an apparatus, 10, for practicing embodiments of the method of the present invention is shown. Signal source, 12, provides a chosen ultrasonic signal, amplified by amplifier, 14, to one or more transmitting transducers, 16, shown mounted at one end of a linear pipe section or vessel segment, 18. Acoustic signals having propagated through pipe or vessel section 18 are detected by receiving transducer, 20, disposed at the opposite end of the pipe or vessel section 18 from transmitting transducer 16. The electrical signal generated by receiving transducer 20 is amplified by amplifier, 22, and filtered by filter, 24, before being directed to signal receiver, 26, is synchronized (triggered with a specific time delay with respect to) with signal source 12. These signals are processed by signal receiver 26, and the processed signal is directed to computer, 28, for data acquisition and analysis. Computer 28 also controls elements 12, 14, 22, 24, and 26.

Separate pre-amplifier and filter modules for may be used for each transducer, all electronic components being wired together using coaxial cables or USB cables. In this configuration, re-connection of the wires is required for using any transducer as transmit or receive sensor, although all transducers are identical and can serve as transmit or receive sensors without any modification. A network of sensors and communication apparatus, all wirelessly connected to a central computer for instrument control, data acquisition, and data analysis, may be used to accommodate multiple transducers. Each sensor would have a unique RFID tag, and an integrated electronics module for both transmit and receive functionality. Such dual functionality would make the system readily re-configurable, and enhance the robustness against defective or failed sensor components. Power for the sensors and integrated modules may be provided by batteries, and charging energy might be harvested from solar power, as an example.

Vessels may be monitored in segments, where each segment has relatively uniform wall thickness and physical proximity. If the vessel segments have significant non-uniformities, such as welded ribs or other physical attachments, then (more than one) transmit transducer and (more than one) receive transducer may be used. The number of transmit and receive transducers will be commensurate with the non-uniformity of the segment, and the areal size of the segment. Increasing the number of transmit transducers will permit more uniform acoustic excitation, and sampling of "all" parts of the segment will lead to better sensitivity, selectivity, and robustness of detection of corrosion and other defects. Additionally, the increased number of receive transducers will introduce redundancy to the system, which will make the present method more reliable and robust.

Figure 1B:
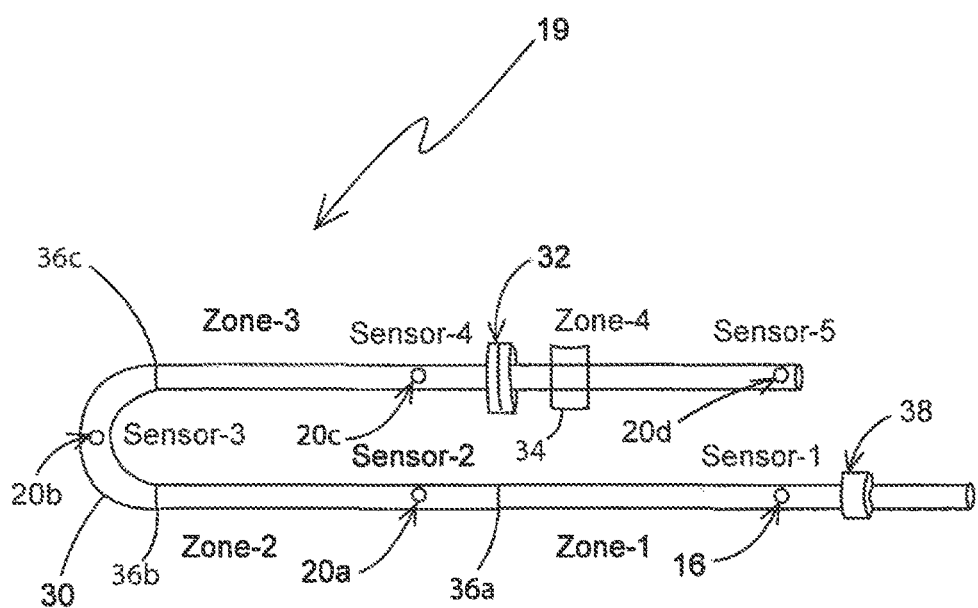
FIG. 1B is a schematic representation of a more complex pipe configuration, for which the present apparatus may be employed.

FIG. 1B is a schematic representation of a pipe assembly having a more complex series of attached pipe sections, 19, (105-ft-long, 8-in-diameter schedule-40 carbon steel pipe with two 90°-elbows, 8 welded-joints, and 1 pair of flanges, the assembly supported by 10 stands) that may be monitored in accordance with embodiments of the present invention. Five, evenly spaced (approximately 25 ft. apart) transducers 16, 20a, 20b, 20c, and 20d, are permanently-attached along an about 100-ft section of the pipe, having curved section, 30 (two 90°-elbows). Although only one transducer 16 is identified as a transmitting transducer (FIG. 1A), all five transducers may both transmit and receive. Zones marked 1 through 4 define minimum interrogation areas of the pipe (about 25 ft. in length) using the apparatus illustrated in FIG. 1A, when nearest sensors are used for transmit and receive. For example, Zone-4 is an approximately 25 ft. section of the pipe assembly between Sensor-4, 20c, and Sensor-5, 20d, and includes flange connection, 32, and material removal area, 34. Larger lengths areas may be interrogated by using further-separated sensors. For example, all four zones may be interrogated at the same time by using Sensor-1, 16, as the excitation (transmit) sensor and Sensor-5, 20d, as the receive sensor. Three welded sections, 36a-36c, are also illustrated, as is commercial sensor array collar, 38.

Existing temperature compensation methods, such as optimal signal stretch (OSS) method, estimate a stretch factor through multiple iterations of all expected outcomes, which is computationally inefficient. Moreover, these methods are best suited for simple geometries having pure time-stretch effects, whereas the embodiments of the present method are applicable to more complex geometries having time-stretch as well as signal distortion effects.

As stated above, each attached transducer may function both as a transmit and a receive transducer, thus eliminating the need to attach extra transducers in certain neighboring pipe sections or vessel segments when a network of interconnected pipes and vessel segments are to be monitored.

Using multiple sensors along the length of a piping section to monitor that piping segment can lead to additional localization information of where the changes occurred. It is possible to provide some estimate the location of dominant wall loss in a zone by monitoring the amplitude of signal in adjacent zone. Specifically, the amplitude of signal in the adjacent zone decreases as a function of the distance of dominant wall loss from the shared transmitting transducer. Another adjacent effect that could be utilized to estimate the location of dominant wall loss is related to the time of arrival of dominant scattered signals. The delay time of the dominant scattered signal from the neighboring zone is related to the distance of the dominant wall loss area from the transmitting transducer and receive transducer on the other end of the adjacent zone.

A. Embodiments of the Present ND-STFT Method:

(1) One embodiment of the present ND-STFT method includes the following steps:

(a) Select a frequency chirp signal having a signal strength between about 1 and approximately 100 V; a spectral content of between about 10 kHz and about 200 kHz. There are several longitudinal, torsional, and flexural modes (L-, T-, and F-modes, respectively) that support acoustic signal propagation at kHz-MHz frequencies in pipes and vessels having wall thicknesses ranging between ⅛ in. and 4 in. Therefore, between about 1 kHz to about 1 MHz, and more advantageously, between about 10 kHz to about 200 kHz range is effective for acoustic interrogation of corrosion and other defects, because such acoustic modes are sensitive to various defects and mechanical perturbations, and also because they do not significantly dissipate over long length propagation, up to hundreds of feet). A duration between approximately 0.1 ms and about 10 ms, and a repetition rate between approximately 10 ms and approximately 1000 ms, are useful for the interrogating excitation signal;

(a) Time-Average (between about 64 and about 4096 repetitions), and Filter (band-pass, and/or low-pass, and/or high-pass) the first received signal (baseline or reference signal);

(b) Remove the DC component from the first received signal so that only AC components remain;

(c) Repeat steps (a)-(c) to obtain a second received signal (monitoring signal or measurement);

(d) Normalize the signal strength of the first received signal and the second received signal so that the strongest component in either signal equals a chosen number, for example, 1

(e) Perform STFT of the time-averaged, first and second AC received signals with chosen time and frequency window sizes, and time steps, (for example, a Hamming Window size of 1024, and a step size of 32 with a frequency increment of 1 kHz and a time increment of 100 ns were used for 20-ft-long, 2¾ in.-diameter (¼ in.-wall-thickness) pipe);

(f) Take the difference between normalized first and second STFT 2D surface/contour maps obtained in a similar manner to that of the baseline or reference STFT at a chosen time, T, when a perturbation is expected, or during routine testing and the baseline or reference ND-STET at T=0, forming a new STFT 2D surface/contour map, which illustrates energy loss and energy gain among acoustic modes;

(g) Identify specific frequency-time mode pair(s) in the 2D map where scattering event(s) (or set(s) of events) can be discerned (a scattering event will appear as a bump, or crest (positive signal), with a corresponding dip or trough (negative signal), in the ND-STFT map); and (h) Calculate the amplitude difference between crest of the feature having the maximum height and the trough of the corresponding feature having the minimum depth in the ND-STFT map (that is, the maximum signal difference).

Using the maximum signal difference (or, ND-STFT Signal Range) calculated in accordance with step 8 in the embodiment of the method described hereinabove, is one way of mapping the 2-Dimensional data into a scalar. As will be described in the EXAMPLES, this approach has been successfully used to quantify the level of corrosion or defect in a pipe section or vessel segment, and has been found to yield a monotonic, near-linear relationship between the level of mechanical perturbation (material loss or material addition) and ND-STFT Signal Range for pipes and vessels.

Other mapping methods are contemplated by the present inventors. As an example, to identify specific frequency-time mode pair(s) (scattering event(s) and corresponding crests and troughs) in the 2D, ND-STFT map, a correlation method may be employed as follows:

(2) (a) Perform a 2D auto-correlation on the 2D, ND-STFT surface contour map with the first dimension being time, and the other being frequency, whereby a 2D auto-correlation map is created;

(b) Identify "auto-correlation crests" as ND-STFT crest-crest or trough-trough correlations, and "auto-correlation troughs" as ND-STFT crest-trough correlations;

(c) Using only the negative "auto-correlation troughs," a "modified 2D auto-correlation map" is created; and (d) Reduce the information in the "modified 2D auto-correlation map" to a single number, auto-correlated scattering standard deviation, by first integrating over frequency dimension, then calculating standard deviation over the time dimension.

The ND-STFT crest-trough correlations, which appear as "auto-correlation troughs" in the 2D auto-correlation map, are of significance since they are directly related to scattering events which are caused by, corrosion, defects, etc.; thus, positive "auto-correlation crests" are numerically removed from the map since they do not contain any direct information of scattering events.

Another embodiment of the present ND-STFT method includes the following steps:

(3) (a) Select a frequency chirp signal having a signal strength between about 1 and approximately 100 V; a spectral content of between about 1 kHz and about 1 MHz, or more advantageously between about 10 kHz and about 200 kHz (There are several longitudinal, torsional, and flexural modes (L-, T- and F-modes, respectively) that support acoustic signal propagation at kHz-MHz frequencies in pipes and vessels having wall thicknesses ranging between ⅛ in. and 4 in. Therefore, the 10 kHz to 200 kHz range is effective for acoustic interrogation of corrosion and other defects, because such acoustic modes are sensitive to various defects and mechanical perturbations, and also because they do not significantly dissipate over long length propagation, up to hundreds of feet). A duration between approximately 0.1 ms and about 10 ms; and a repetition rate between approximately 10 ms and approximately 1000 ms, are useful as parameters for the interrogating excitation signal;

(b) Time-Average (between about 64 and about 4096 repetitions), and Filter (band-pass, and/or low-pass, and/or high-pass) the first received signal (baseline or reference signal);

(c) Remove the DC component from the received signal so that only AC components remain;

(d) Repeat steps (a)-(c) to obtain a second received signal (later monitoring measurement) obtained in a similar manner to that of the baseline or reference signal at a chosen time, T, when a perturbation is expected, or during routine testing, and the baseline or reference at T=0;

(e) Normalize the signal strengths of the first and second received signals so that the strongest component of each equals a chosen number, for example, 1

(f) Take the difference between the second received signal and the baseline signal, forming a "difference signal" at a chosen time, T, when a perturbation is expected, or during routine testing;

(g) Perform STFT of the "difference signal" with chosen time and frequency window sizes, and time steps, (for example, a Hamming Window size of 1024, and a step size of 32 with a frequency increment of 1 kHz and a time increment of 100 ns were used for 20-ft-long, 2¾ in.-diameter (¼ in.-wall-thickness) pipe);

(h) Calculate "Normalized Actionable Output" (a scalar number) from the two-dimensional STFT array, first, by calculating standard deviation of the STFT array along the time-axis for each frequency (one-dimensional array), and sum over the thus calculated, one-dimensional standard deviation array to obtain the scalar.

B. Temperature Compensation:

As stated above, ultrasonic waves penetrate through the thickness of structural elements and can travel long-distances, allowing interrogation of large areas all at once by using a small number of spatially-distributed ultrasonic sensors, with damage being detected by baseline subtraction. When environmental and operational conditions change, the propagating medium and ultrasonic wave behavior also changes, limiting the effectiveness of baseline comparison in distinguishing damage from environmental and operational effects. The most ubiquitous environmental effect is temperature change. Many methods have been developed and implemented to compensate for temperature in structural monitoring applications, with varying effectiveness under different conditions. In accordance with the teachings of embodiments of the present methods effective temperature compensation is provided for a broad set of tested conditions: 1) ultrasonic excitation with multiple modes, or hybridized modes, in specular and diffuse regimes; 2) ultrasonic propagation in homogeneous and non-homogenous media involving multiple reflections, and broad spectral and wide temporal range signals; and 3) autonomous compensation with a wide range of global and local temperature fluctuations in the interrogated medium without the need to know the actual global or local temperatures.

Embodiments of the present method for temperature compensation are effective for: single as well as multiple and hybridized modes; homogeneous and inhomogeneous media, with a wide range of reflective components; and in the presence of both global and local temperature variations. No single time-stretch factor is sufficient to adequately compensate for temperature effects in a real-world monitoring system, where there will be local and global temperature variations, and realistic structures will have varying degrees of inhomogeneities (leading to corresponding varying amounts of reflections), and will support a variety of modes for ultrasonic wave propagation with varying temperature effects. Thus, the present method generates an appropriate set of time-delay factors to replace the single time-stretch factor that is commonly used in other temperature compensation methods.

When ultrasonic signals arrive at the receiving sensor, they accumulate all the phase shifts that they encounter in the pipe, and all the modes and reflections, thus phase-shifted, combine to form a complex waveform. This waveform is distributed in time. As will be described below, this time-distributed waveform is divided into bins, each bin of a waveform segment being temperature compensated using a single delay factor. The delay factor for each bin is calculated using cross-correlation between the real-time measured data and the previously measured baseline data, without any direct knowledge of local or global change of temperature in the interrogated medium. The time delay for each bin is the peak position of the cross correlation function. Once each bin is temperature compensated, the bins are combined to form a temperature-compensated waveform.

The minimum size of the bins is determined by the minimum wavelength of the ultrasonic waves of interest, and the maximum size of the bins is determined by the time delay dependence of the phase shift that is to be compensated. In practice, bin sizes are empirically or theoretically optimized; it is usually between approximately 0.01 ms and about 1 ms, for adequate temperature compensation in a practical USHM system. The number of bins also depends on the specifics of the monitoring system. In practice, it may vary between about 10 and about 1000.

Embodiments of the present method will provide sensitive and selective diagnostics for pipes and vessels for changes including:
1. Water accumulation on pipe/vessel walls, which could be a precursor to corrosion;
2. Significant paint chipping or major insulation degradation, which again could be a precursor to corrosion;
3. Excessive pipe sagging, which could lead to microcracking and other mechanical degradations;
4. Solid object leaning strongly against a pipe or vessel wall, which could lead to localized degradation of pipe integrity; and
5. Internal clogging of pipe walls or blockage of pipe, which could lead to flow problems and/or internal corrosion, etc.

Volume changes of less than 0.1% in 16"×2" pipe wall sections of 50-ft-long pipe were detected.

Having generally described the present invention, the following EXAMPLES provide additional details. EXAMPLES 1-4 describe ND-STFT method (1).

Example 1

Figure 2:
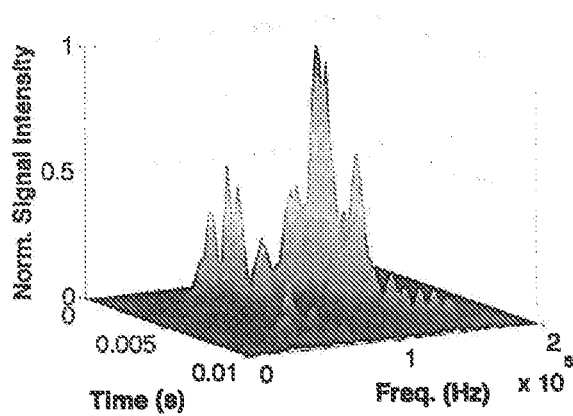
FIG. 2 shows the received signal after a linear chirp was transmitted 20-ft along an empty corroded pipe having 10-in. diameter, and ½-in. wall thickness.
Figure 3:
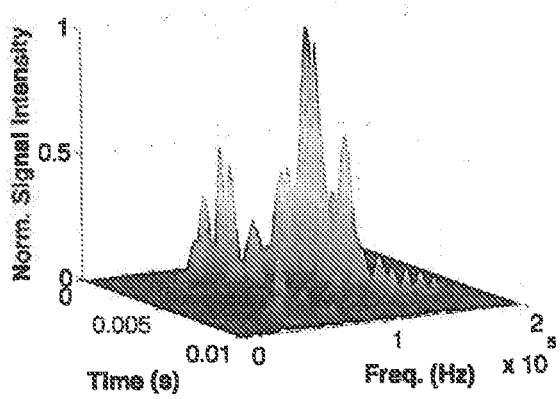
FIG. 3 shows the same received signal after a linear chirp signal was transmitted 20-ft along the empty corroded pipe described in FIG. 2, hereof, but perturbed by attaching, 12 small magnets on the pipe wall, thereby generating a local volume change of about 3% on the pipe wall.

The effect of material addition through attachment of small magnets on pipe walls is demonstrated:

FIG. 2 shows the received signal after 20-ft transmission along an empty corroded pipe having 10" diameter, and ½" wall thickness, and used as a baseline. The transmitted linear chirp, was 10 V peak-to-peak, between 5 kHz and 200 kHz, with 1 ms duration, and repeated every 100 ms. FIG. 3 shows the same received signal after 20-ft transmission along the empty corroded pipe with 10" diameter, and ½" wall thickness mentioned in FIG. 2, hereof, but perturbed by attaching, 12 small magnets on the pipe wall generating a local volume change of about 3% on the pipe wall. The two normalized signals show, at first impression, little difference in the time/frequency domain.

Figure 4A:
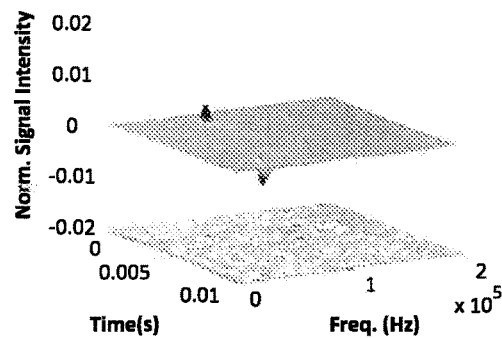
FIGS. 4A-4C are graphs of the Normalized-Difference Short-Time-Fourier-Transform (ND-STFT) signal calculated by taking the difference between the first (baseline) and the second (perturbed) signal intensities shown in FIGS. 2 and 3, hereof, for 2, 4 and 12 attached magnets, respectively.
Figure 4B:
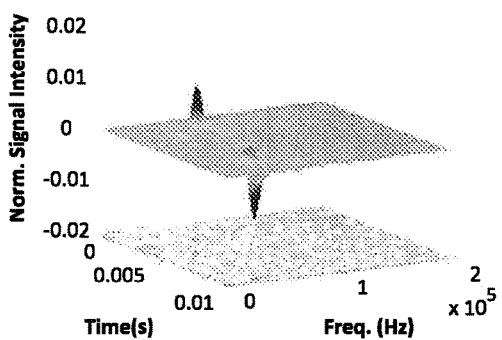
Figure 4C:
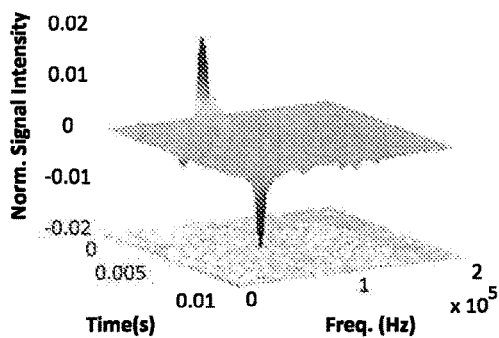
Figure 5:
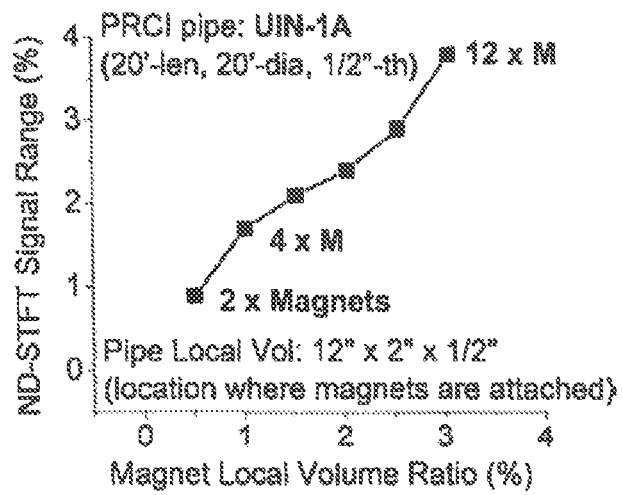
FIG. 5 is a graph of the difference of the maximum height and the minimum depth in the ND-STFT map, as a function of magnets attached.

FIGS. 4A-4C are graphs of the ND-STFT signal calculated by taking the difference between the first (baseline) and the second (perturbed) signal intensities shown in FIGS. 2 and 3 discussed hereinabove, for 2, 4 and 12 attached magnets, respectively, while FIG. 5 is a graph of the difference of the maximum height and the minimum depth in the ND-STFT map (that is, the maximum signal difference), as a function of magnets attached.

Example 2

Figure 6:
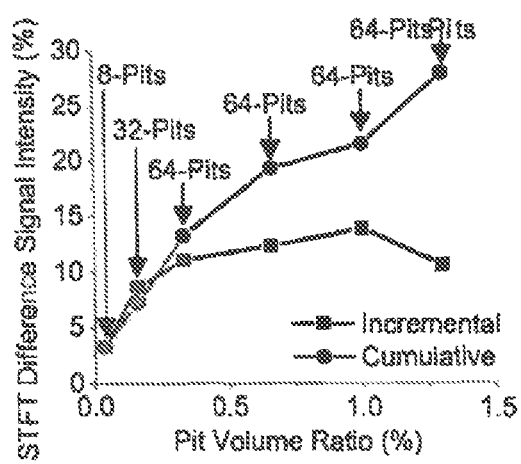
FIG. 6 is a graph of the difference in the maximum height and the minimum depth in the ND-STFT map (that is, the maximum signal difference), or, equivalently, the STFT difference signal intensity, as a function of material removed (or, pit volume ratio) for a signal having traveled along an uncorroded pipe having 20-ft. length, 2¾-in. diameter, and ¼-in, wall thickness.

The effect of material removal through drilling of pockets on pipe walls for an uncorroded pipe having 20'-length, 2¾"-dia, ¼"-wall thickness:

FIG. 6 is a graph of the difference in the maximum height and the minimum depth in the ND-STFT map (that is, the maximum signal difference), or, equivalently, the STFT difference signal intensity, as a function of material removed (or, pit volume ratio).

Example 3

Figure 7:
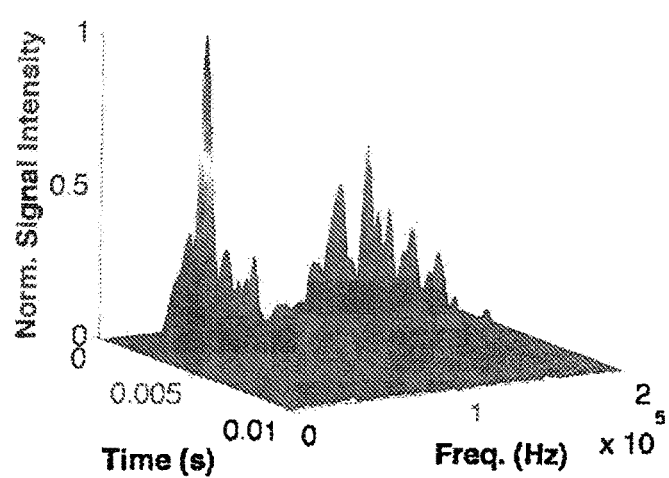
FIG. 7 is a graph of the received signal with no perturbation (baseline) having traveled the length of a cylindrical vessel, wherein 4 transmitting transducers and 1 receiving transducer are employed.
Figure 8A:
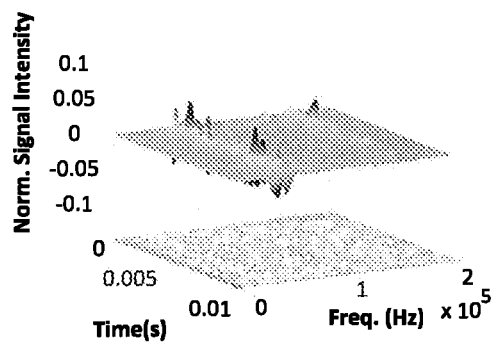
FIGS. 8A-8C are graphs of the ND-STFT difference signal between the baseline and after 0.2 cc, 0.6 cc and 1.2 cc of material, respectively, was removed by grinding.
Figure 8B:
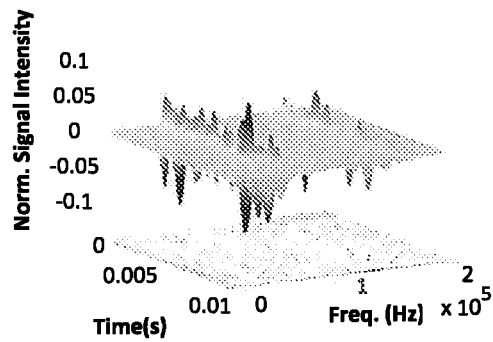
Figure 8C:
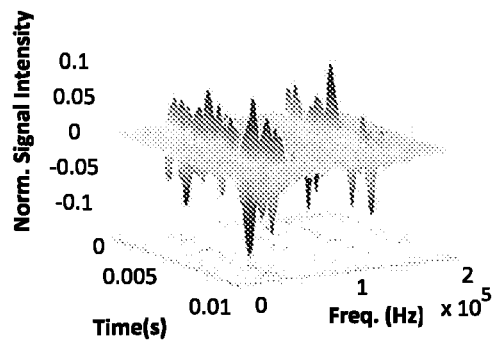

The effect of material removal through grinding holes on vessel walls (in this case vessel segment is the entire vessel), wherein 4 transmitting transducers and 1 receiving transducer were employed:

FIG. 7 is a graph of the received signal with no perturbation (baseline), while FIGS. 8A-8C are graphs of the ND-STFT signal (difference between the baseline and after 0.2 cc, 0.6 cc and 1.2 cc of material, respectively, was removed by grinding.

Figure 9:
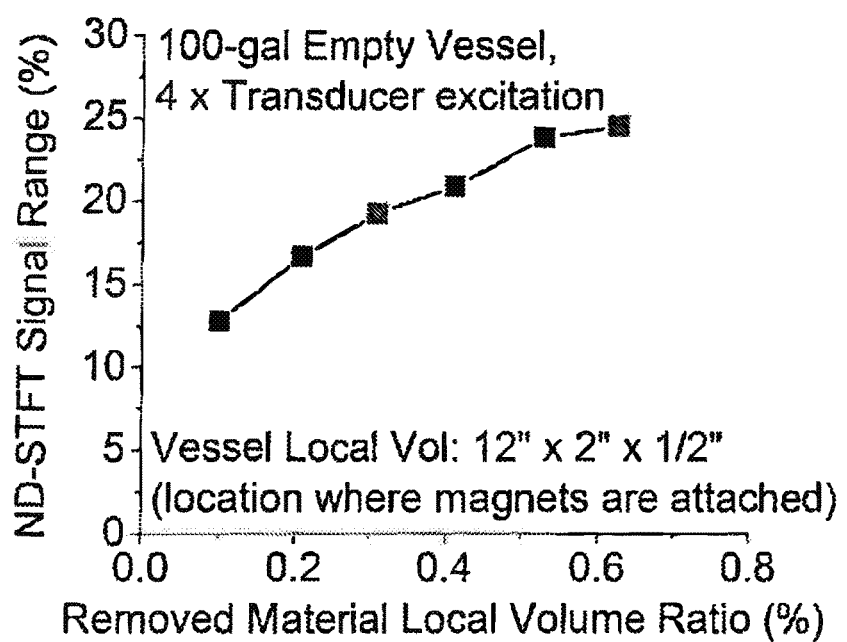
FIG. 9 is a graph of the maximum height and the minimum depth of the ND-STFT map (i.e., maximum signal difference), as a function of removed material from an empty vessel.

FIG. 9 is a graph of the difference between the maximum height and the minimum depth of the ND-STFT map (that is, the maximum signal difference), as a function of removed material for an empty vessel.

Example 4

Figure 10:
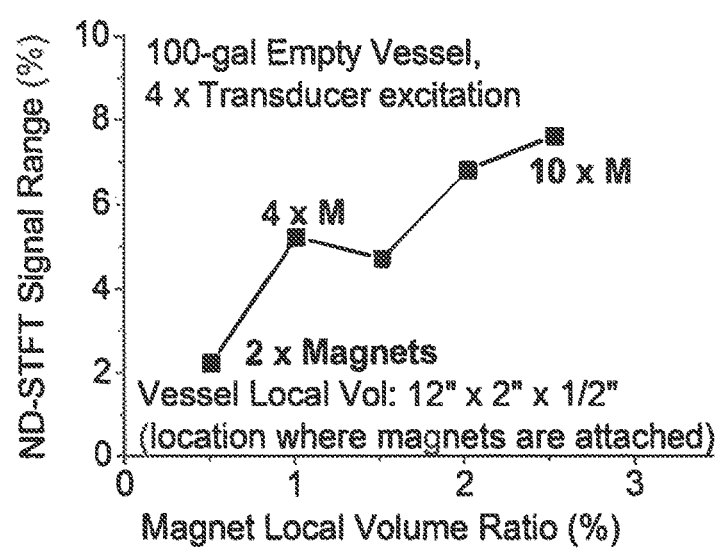
FIG. 10 is a graph of the difference between the maximum height and the minimum depth of the ND-STFT map (that is, the maximum signal difference), as a function of added material (magnets) for an empty vessel.

The effect of material addition through attachment of magnets on vessel walls (in this case vessel segment is the entire vessel, wherein 4 transmitting transducers, and 1 receiving transducer were employed:

FIG. 10 is a graph of the difference between the maximum height and the minimum depth of the ND-STFT map (that is, the maximum signal difference), as a function of added material (magnets) for an empty vessel.

EXAMPLE 5 illustrates the use of temperature-compensated ND-STFT method (3).

Example 5

Examples of temperature compensation are given below for experiments conducted on the approximately 105-ft-long pipe assembly. In FIGS. 11A, 11B, 12A, 12B, 13A, and 13B, the 25-ft sensor distance is for transducers 20a, performing as a transmitter and 20b, performing as a receiving transducer: the 50-ft sensor distance is for transducers 20b, performing as a transmitter and transducer 20d, performing as a receiver; and the 105-ft sensor distance is for transducers 16 and 20d.

Figure 11A:
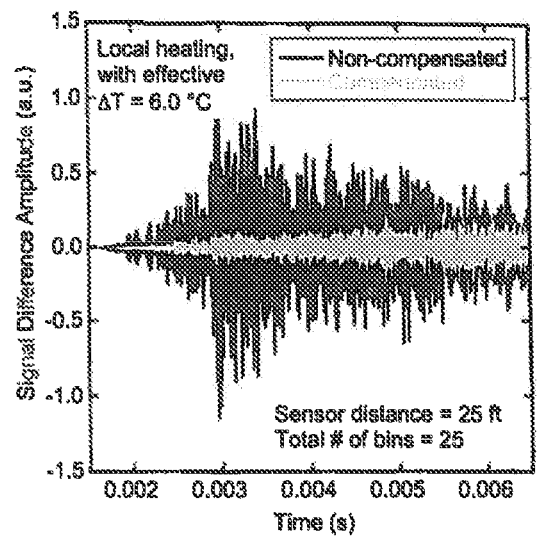

FIG. 11A is a graph of the signal difference amplitude as a function of time for both temperature compensated and non-temperature-compensated signals in a situation where there has been no material loss, conversion, or addition between the measurements. The non-temperature-compensated signal difference is calculated by subtracting a reference (baseline) signal from a subsequent measurement signal in the time-domain, whereas compensated signal difference is calculated by subtracting reference signal from a temperature-compensated subsequent measurement signal, as described above. As may be observed, in the FIG. 11A, the amplitude of the difference signal is reduced significantly after temperature compensation; that is, the spurious signal due to temperature variation is significantly reduced. Thus, temperature compensation reduces the spurious signal level, thereby resulting in an improved sensitivity limit for detection of material gain or loss.

Figure 11B:
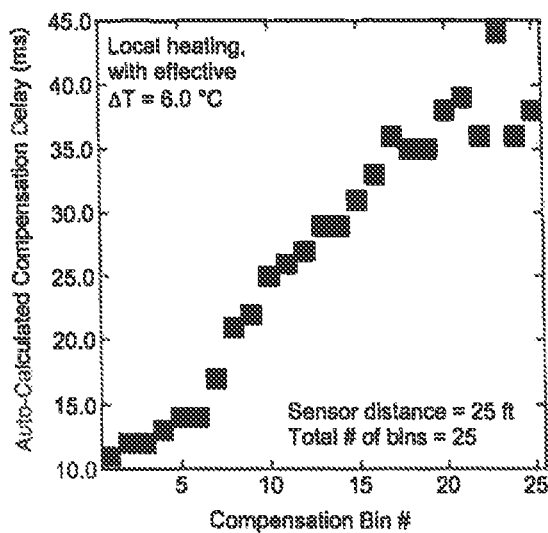
FIG. 11B is a graph illustrating the specific delay times that are calculated for each bin (for a total of 25 bins) for the data shown in FIG. 11A.

FIG. 11B is a graph illustrating the specific delay times that are calculated for each bin (for a total of 25 bins) for the data shown in FIG. 11A. As mentioned above, these delay times are used to shift the time-domain waveforms in each bin, and the temperature-compensated signal is generated from a combination of such compensated waveforms from each bin, FIGS. 11A and 11B therefore show the effect of temperature compensation on the signals, and the specific delays that were calculated for each bin to achieve this result.

Figure 12A:
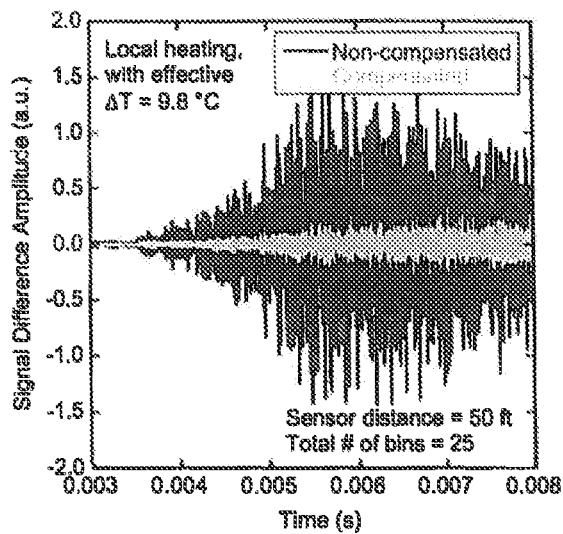
Figure 12B:
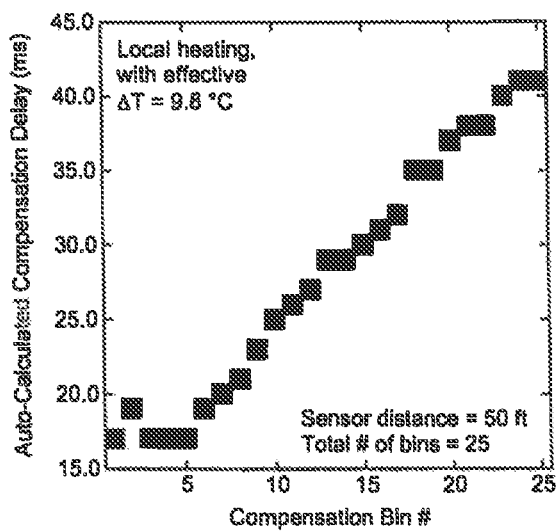
FIG. 12B is a graph illustrating the specific delay times that are calculated for each bin (for a total of 25 bins) for the data shown in FIG. 12A.
Figure 13A:
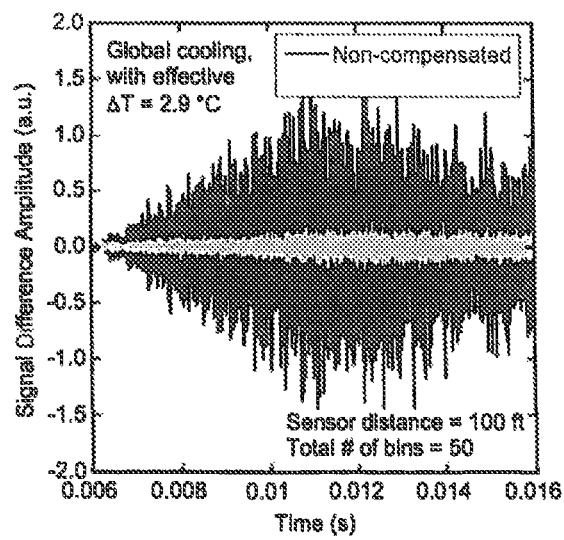
Figure 13B:
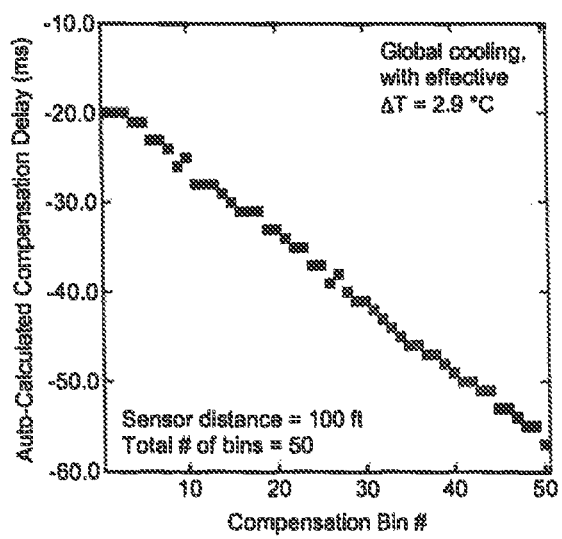
FIG. 13B is a graph illustrating the specific delay times that are calculated for each bin (for a total of 50 bins) for the data shown in FIG. 13A.

FIGS. 12A and 12B are graphs illustrating the same results for a 50 ft. transducer distance, using 25 bins, and FIGS. 13A and 13B are graphs illustrating the same results for a 100 ft transducer distance using 50 bins, respectively. The slopes for FIGS. 11B and 12B are positive because the temperature variation is positive, whereas that for FIG. 13B is negative because the temperature variation is negative.

Effectiveness of temperature compensation can be quantified by using sensitivity improvement factor (SW) which is defined as the ratio of spurious difference signal strength without compensation to difference spurious signal strength with compensation. The TABLE summarizes SIF values for different pipes, at various transducer-to-transducer distances, and for several global and local temperature changes.

(d) Repeat steps (a)-(c) to obtain a second received signal (later monitoring measurement);
(e) Normalize the signal strengths of the first received signal and the second received signal so that the strongest component of either signal equals a chosen number, for example, 1;
(f) Perform temperature compensation of the received signal by comparing it to the baseline signal;
(g) Perform STFT of the time-averaged, first and second AC received signals with chosen time and frequency window sizes, and time steps, (for example, a Hamming Window size of 1024, and a step size of 32 with a frequency increment of 1 kHz and a time increment of 100 ns were used for 20-ft-long, 2¾ in.-diameter (¼ in.-wall-thickness) pipe);
(h) Take the difference between normalized first and second STFT 2D surface/contour maps obtained in a similar manner to that of the baseline or reference STFT at a chosen time, T, when a perturbation is expected, or during routine testing and the baseline or reference ND-STFT at T=0, forming a new STFT 2D surface/contour map, which illustrates energy loss and energy gain among acoustic modes;
(i) Identify specific frequency-time mode pair(s) in the 2D map where scattering event(s) (or set(s) of events) can be discerned (a scattering event will appear as a bump, or crest (positive signal), with a corresponding dip or trough (negative signal), in the ND-STFT map); and

TABLE

| TYPE | DIA | DIST | TEMP | $\Delta T$ | SPAN | NUMB | SIF |
|---|---|---|---|---|---|---|---|
| Uniform | 2 in | 25 ft | global | 4° C. | 5 ms | 25 | 18 |
| Uniform | 2 in | 25 ft | local | 20° C. | 5 ms | 50 | 75 |
| Non-uniform | 8 in | 25 ft | global | 3° C. | 5 ms | 25 | 29 |
| Non-uniform | 8 in | 50 ft | global | 2.5° C. | 5 ms | 50 | 52 |
| Non-uniform | 8 in | 100 ft | global | 3° C. | 10 ms | 50 | 58 |
| Non-uniform | 8 in | 25 ft | local | 6° C. | 5 ms | 25 | 26 |
| Non-uniform | 8 in | 50 ft | local | 10° C. | 5 ms | 25 | 31 |

Key:
TYPE: Type of pipe section; uniform (straight) vs. non-uniform (with bends, elbows, flange connections, etc.)
DIA: Schedule-40 pipe diameter
DIST: Sensor-to-sensor distance
TEMP: Temperature change type; global (relatively uniform in the interrogated region) vs. local (large gradient within the interrogated region)
$\Delta T$: Effective temperature change
SPAN: Time span of received signal to be compensated
NUMB: Total number of bins used for compensation
SIF: Sensitivity Improvement Factor With temperature correction, embodiment (1) of the present ND-STFT method includes the following steps:
(a) Select a frequency chirp signal having a signal strength between about 1 and approximately 100 V; a spectral content of between about 10 kHz and about 200 kHz, a duration between approximately 0.1 ms and about 10 ms, and a repetition rate between approximately 10 ms and approximately 1000 ms;
(b) Time-Average (between about 64 and about 4096 repetitions), and Filter (band-pass, and/or low-pass, and/or high-pass) the first received signal (baseline or reference signal);
(c) Remove the DC component from the first received signal so that only AC components remain;

(j) Calculate the amplitude difference between crest of the feature having the maximum height and the trough of the corresponding feature having the minimum depth in the ND-STFT map (that is, the maximum signal difference).

And with temperature correction, embodiment (3) of the present ND-STFT method includes the following steps:
(a) Select a frequency chirp signal having a signal strength between about 1 and approximately 100 V; a spectral content of between about 1 kHz and about 1 MHz or more advantageously between about 10 kHz and about 200 kHz; a duration between approximately 0.1 ms and about 10 ms; and a repetition rate between approximately 10 ms and approximately 1000 ms, as the interrogating excitation signal;
(b) Time-Average (between about 64 and about 4096 repetitions), and Filter (band-pass, and/or low-pass, and/or high-pass) the received signal;
(c) Remove DC component of the received signal so that only AC components remain;
(d) Normalize the signal strength for both the received signal and the reference signal so that the strongest component equals a chosen number for both, 1, as an example;
(e) Perform temperature-compensation of the received signal by comparing it to baseline signal;
(f) Take the difference between the temperature-compensated received signal and the baseline or reference signal, forming difference signal at a chosen time, T, when a perturbation is expected, or during routine testing;
(g) Perform STFT of the difference signal with chosen time and frequency window sizes, and time steps; and
(h) Calculate the actionable output (a scalar number which is used to determine whether remedial action needs to be taken, such as pipe replacement or repair, as examples) from the two-dimensional STFT array, by calculating standard deviation of the STFT array along the time-domain for each frequency (one-dimensional array), and then summing over the thus calculated one dimensional standard deviation array at each frequency to obtain the scalar.

Experimental evidence shows that this procedure adequately compensates for temperature effects when: different modes are present, the medium is not homogeneous, there are significant scattered waves, and there are local as well as global temperature changes, while having little spurious effect on waveform changes due to simulated or real damage.

Figure 14:
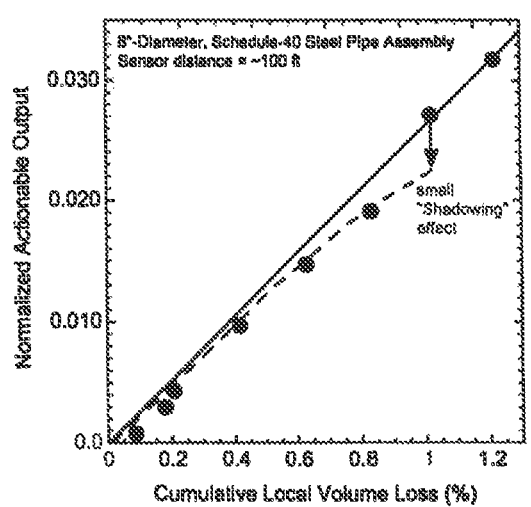
FIG. 14 is a graph of the normalized actionable output calculated by mapping acoustic amplitude, time and frequency data, which may be used as a guide for determining whether action needs to be taken relative to pipe safety, as a function of cumulative local volume loss.

FIG. 14 is a graph of the normalized actionable output (scalars) as a function of cumulative local volume loss for the 105-ft-long pipe assembly described in FIG. 1B hereof, for sensor-to-sensor distance of 100 ft. The volume loss on the pipe wall was simulated by removing material from the pipe wall with a grinder. Between 0.1 and 0.8% local volume loss the material was removed along the axis of the pipe in the shape of square pockets, with small shadowing effect. The data for 1% and 1.2% were obtained when material was removed circumferentially with respect to last square pocket. In this case, no significant shadowing effect is observed. These results show that embodiments of the present method are applicable for long distances in the presence of significant non-uniformities (flanges, elbows, bends, stand connections, etc.), and are linear over a wide range (0.1 to 1% local volume loss). The sensitivity limit, which is about 0.1% volume loss in this example, is determined by the effect of operational environment on the temperature variation and the effectiveness of the present temperature method. This sensitivity limit of 0.1% local volume loss is preserved for environmental temperature fluctuations of ±3° C. For a temperature variation of ±10° C., this sensitivity limit expands to about 0.5%.

Embodiments of the present method may be used for monitoring a wide range of engineered structures, such as vessels, pipes, airplanes, railroads, bridges, and buildings.

The foregoing description of the invention has been presented for purposes of illustration and description and is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A method for detection and monitoring changes in an elongated metallic structure having a wall and an exterior surface, comprising:
   placing at least one acoustic transmitting transducer in vibrational communication with the exterior surface of said metallic structure;
   placing at least one receiving transducer in vibrational communication with the exterior surface of said metallic structure and spaced apart a chosen length from said at least one transmitting transducer;
   generating acoustic frequency chirp signals having a selected signal strength, spectral content, and duration;
   directing the chirp signals to said at east one transmitting transducer;
   producing a baseline signal by:
      receiving the vibrational signals generated in the wall of said metallic structure in response to the chirp signal by the receiving transducer;
      averaging a chosen number of received vibrational signals; and
      removing any DC component from the averaged received signals;
   producing a monitoring signal by:
      receiving the vibrational signals generated in the wall of said metallic structure in response to the chirp signal by the receiving transducer;
      averaging a chosen number of received vibrational signals; and
      removing any DC component from the averaged received signals;
      normalizing the monitoring signal to the baseline signal, whereby a maximum value of each of the baseline signal and the monitoring signal is equal to a selected value;
   performing short-time Fourier Transforms of the baseline and monitoring signals using chosen time and frequency window sizes, and time steps;
      taking the difference between the normalized monitoring signal and the normalized baseline signal, forming thereby a two-dimensional contour map;
   identifying at least one frequency-time mode pair in the contour map, where one feature of the at least one frequency-time mode pair has a maximum positive value and the corresponding feature of the at least one frequency-time mode pair has a maximum negative value; and
   calculating the amplitude difference between maximum positive value and the maximum negative value.

2. The method of claim 1, further comprising the step of performing temperature compensation of the monitoring signal using the baseline signal as a comparison signal after said step of normalizing the monitoring signal to the baseline signal, thereby producing a temperature-compensated monitoring signal.

3. The method of claim 2, wherein said step of performing temperature compensation comprises:
   dividing the monitoring signal into a chosen number of equal-duration time bins as a function of time;

calculating the cross-correlation function for the monitoring signal and the baseline signal for each time bin;
determining a time shift for each time bin by locating a peak of the cross correlation function for each time bin; and
assigning a value of the monitoring signal to each bin corresponding to a value of the monitoring signal at the shifted time for that bin, whereby a temperature-compensated monitoring signal is generated.

4. The method of claim 1, further comprising the step of filtering the received vibrational signals after said step of receiving the vibrational signals generated in the wall of said metallic structure in response to the chirp signal for both of said steps of producing a baseline signal and for producing a monitoring signal.

5. The method of claim 1, wherein the chirp signals have a spectral content of between about 1 kHz and about 1 MHz.

6. The method of claim 1, wherein said elongated metallic structure comprises at least one structure chosen from a length of metallic pipe, a metallic pipe assembly, a flange, an elbow, a tee, a reducer, a weld, a vessel, a storage tank, and a storage container.

7. The method of claim 1, wherein the monitoring signal is produced subsequent to when the baseline signal is produced.

8. The method of claim 1, further including the step of comparing the change in the monitoring signal for two adjacent pipe segments, whereby the localization of changes to said metallic structure within one of the segments is determined.

9. A method for detection and monitoring changes in an elongated metallic structure having a wall and an exterior surface, comprising:
placing at least one acoustic transmitting transducer in vibrational communication with the exterior surface of said metallic structure;
placing at least one receiving transducer in vibrational communication with the exterior surface of said metallic structure and spaced apart a chosen length from said at least one transmitting transducer;
generating acoustic frequency chirp signals having a selected signal strength, spectral content, and duration;
directing the chirp signals to said at least one transmitting transducer;
producing a baseline signal by:
  receiving the vibrational signals generated in the wall of said metallic structure in response to the chirp signal by the receiving transducer;
  averaging a chosen number of received vibrational signals; and
  removing any DC component from the averaged received signals;
producing a monitoring signal by:
  receiving the vibrational signals generated in the wall of said metallic structure in response to the chirp signal by the receiving transducer;
  averaging a chosen number of received vibrational signals; and
  removing any DC component from the averaged received signals;
normalizing the monitoring signal to the baseline signal, whereby a maximum value of each of the baseline signal and the monitoring signal is equal to a selected value;
taking the difference between the monitoring signal and the baseline signal; forming a difference signal;
performing short-time Fourier transform of the difference signal using chosen time and frequency window sizes, and time steps, forming thereby a two-dimensional array in time and frequency;
calculating the standard deviation of the short-time Fourier transform array along the time-axis for each frequency; and
summing the standard deviations as a function of frequency.

10. The method of claim 9, further comprising the step of performing temperature compensation of the monitoring signal using the baseline signal as a comparison signal after said step of normalizing the monitoring signal to the baseline signal, thereby producing a temperature-compensated monitoring signal.

11. The method of claim 10, wherein said step of performing temperature compensation comprises:
dividing the monitoring signal into a chosen number of equal-duration time bins as a function of time;
calculating the cross-correlation function for the monitoring signal and the baseline signal for each time bin;
determining a time shift for each time bin by locating a peak of the cross correlation function for each time bin; and
assigning a value of the monitoring signal to each bin corresponding to a value of the monitoring signal at the shifted time for that bin, whereby a temperature-compensated monitoring signal is generated.

12. The method of claim 9, further comprising the steps of filtering the received vibrational signals after said step of receiving the vibrational signals generated in the wall of said metallic structure in response to the chirp signal for both of said steps of producing a baseline signal and for producing a monitoring signal.

13. The method of claim 9, wherein the chirp signals have a spectral content of between about 1 kHz and about 1 MHz.

14. The method of claim 9, wherein said elongated metallic structure comprises at least one structure chosen from a length of metallic pipe, a metallic pipe assembly, a flange, an elbow, a tee, a reducer, a weld, a vessel, a storage tank, and a storage container.

15. The method of claim 9, wherein the monitoring signal is produced subsequent to when the baseline signal is produced.

16. The method of claim 9, further including the step of comparing the change in the monitoring signal for two adjacent pipe segments, whereby the localization of changes to said metallic structure within one of the segments is determined.

17. A method for detection and monitoring changes in an elongated metallic structure having a wall and an exterior surface, comprising:
placing at least one acoustic transmitting transducer in vibrational communication with the exterior surface of said metallic structure;
placing at least one receiving transducer in vibration communication with the exterior surface of said metallic structure and spaced apart a chosen length from said at least one transmitting transducer;
generating acoustic frequency chirp signals having a selected signal strength, spectral content, and duration;
directing the chirp signals to said at least one transmitting transducer;
producing a baseline signal by:

receiving the vibrational signals generated in the wall of said metallic structure in response to the chirp signal by the receiving transducer;
averaging a chosen number of received vibrational signals; and
removing any DC component from the averaged received signals;
producing a monitoring signal by:
receiving the vibrational signals generated in the wall of said metallic structure in response to the chirp signal by the receiving transducer;
averaging a chosen number of received vibrational signals; and
removing any DC component from the averaged received signals;
normalizing the monitoring signal to the baseline signal, whereby a maximum value of each of the baseline and the monitoring signals is equal to a selected value;
performing short-time Fourier Transforms of the baseline and monitoring signals using chosen time and frequency window sizes, and time steps;
taking the difference between the normalized monitoring signal and the normalized baseline signal, forming thereby a two-dimensional contour map;
performing a two-dimensional auto-correlation on the two-dimensional contour map wherein the first dimension being time, and wherein the second dimension is frequency, whereby a two-dimensional auto-correlation map;
identifying auto-correlation crests as crest-crest or trough-trough correlations, and auto-correlation troughs as crest-trough correlations in the two-dimensional auto-correlation map;
creating a modified two-dimensional auto-correlation map using only negative auto-correlation troughs;
integrating over the frequency dimension; and
calculating the standard deviation over the time dimension from the modified two-dimensional auto-correlation map, thereby obtaining a number.

18. The method of claim 17, further comprising the step of performing temperature compensation of the monitoring signal using the baseline signal as a comparison signal after said step of normalizing the monitoring signal to the baseline signal, thereby producing a temperature-compensated monitoring signal.

19. The method of claim 18, wherein said step of performing temperature compensation comprises:
dividing the monitoring signal into a chosen number of equal-duration time bins as a function of time;
calculating the cross-correlation function for the monitoring signal and the baseline signal for each time bin;
determining a time shift for each time bin by locating a peak of the cross correlation function for each time bin; and
assigning a value of the monitoring signal to each bin corresponding to a value of the monitoring signal at the shifted time for that bin, whereby a temperature-compensated monitoring signal is generated.

20. The method of claim 17, further comprising the steps of filtering the received vibrational signals after said step of receiving the vibrational signals generated in the wall of said metallic structure in response to the chirp signal for both of said steps of producing a baseline signal and for producing a monitoring signal.

21. The method of claim 17, wherein the chirp signals have a spectral content of between about 1 kHz and about 1 MHz.

22. The method of claim 17, wherein said elongated metallic structure comprises at least one structure chosen from a length of metallic pipe, a metallic pipe assembly, a flange, an elbow, a tee, a reducer, a weld, a vessel, a storage tank, and a storage container.

23. The method of claim 17, wherein the monitoring signal is produced subsequent to when the baseline signal is produced.

24. The method of claim 17, further including the step of comparing the change in the monitoring signal for two adjacent pipe segments, whereby the localization of changes to said metallic structure within one of the segments is determined.

25. A method for detection and monitoring changes in an elongated setalliic structure having a wall and an exterior surface, comprising:
placing at least one acoustic transmitting transducer in vibrational communication with the exterior surface of said metallic structure;
placing at least one receiving transducer in vibrational communication with the exterior surface of said metallic structure and spaced apart a chosen length from said at least one transmitting transducer;
generating acoustic frequency chirp signals having a selected signal strength, spectral content, and duration;
directing the chirp signals to said at least one transmitting transducer;
producing a baseline signal by:
receiving the vibrational signals generated in the wall of said metallic structure in response to the chirp signal by the receiving transducer;
averaging a chosen number of received vibrational signals; and
removing any DC component from the averaged received signals;
producing a monitoring signal by:
receiving the vibrational signals generated in the wall of said metallic structure in response to the chirp signal by the receiving transducer;
averaging a chosen number of received vibrational signals; and
removing any DC component from the averaged received signals;
normalizing the monitoring signal to the baseline signal, whereby a maximum value of each of the baseline signal and the monitoring signal is equal to a selected value;
performing temperature compensation of the monitoring signal using the baseline signal as a comparison signal, thereby producing a temperature-compensated monitoring signal;
performing short-time Fourier Transforms of the baseline and temperature-compensated monitoring signals using chosen time and frequency window sizes, and time steps;
taking the difference between the normalized monitoring signal and the normalized baseline signal, forming thereby a two-dimensional contour map;
identifying at least one frequency-time mode pair in the contour map indicative of at least one scattering event, where one feature of the at least one frequency-time mode pair has a maximum positive value and the corresponding feature of the at least one frequency-time mode pair has a maximum negative value; and calculating the amplitude difference between maximum positive value and the maximum negative value.

26. The method of claim 25, wherein said step of performing temperature compensation comprises:
dividing the monitoring signal into a chosen number of equal-duration time bins as a function of time;
calculating the cross-correlation function for the monitoring signal and the baseline signal for each time bin;
determining a time shift for each time bin by locating a peak of the cross correlation function for each time bin; and
assigning a value of the monitoring signal to each bin corresponding to a value of the monitoring signal at the shifted time for that bin, whereby a temperature-compensated monitoring signal is generated.

27. The method of claim 25, further comprising the step of filtering the received vibrational signals after said step of receiving the vibrational signals generated in the wall of said metallic structure in response to the chirp signal for both of said steps of producing a baseline signal and for producing a monitoring signal.

28. The method of claim 25, wherein the chirp signals have a spectral content of between about 1 kHz and about 1 MHz.

29. The method of claim 25, wherein said elongated metallic structure comprises at least one structure chosen from a length of metallic pipe, a metallic pipe assembly, a flange, an elbow, a tee, a reducer, a weld, a vessel, a storage tank, and a storage container.

30. The method of claim 25, wherein the monitoring signal is produced subsequent to when the baseline signal is produced.

31. The method of claim 25, further including the step of comparing the change in the monitoring signal for two adjacent pipe segments, whereby the localization of changes to said metallic structure within one of the segments is determined.

32. A method for detection and monitoring changes in an elongated metallic structure having a wall and an exterior surface, comprising:
placing at least one acoustic transmitting transducer in vibrational communication with the exterior surface of said metallic structure;
placing at least one receiving transducer in vibrational communication with the exterior surface of said metallic structure and spaced apart a chosen length from said at least one transmitting transducer;
generating acoustic frequency chirp signals having a selected signal strength, spectral content, and duration;
directing the chirp signals to said at least one transmitting transducer;
producing a baseline signal by:
receiving the vibrational signals generated in the wall of said metallic structure in response to the chirp signal by the receiving transducer;
averaging a chosen number of received vibrational signals; and
removing any DC component from the averaged received signals;
producing a monitoring signal by:
receiving the vibrational signals generated in the wall of said metallic structure in response to the chirp signal by the receiving transducer;
averaging a chosen number of received vibrational signals; and
removing any DC component from the averaged received signals;
normalizing the monitoring signal to the baseline signal, whereby a maximum value of each of the baseline and the monitoring signals is equal to a selected value;
performing temperature compensation of the monitoring signal using the baseline signal as a comparison signal, thereby producing a temperatures compensated monitoring signal;
taking the difference between the temperature-compensated monitoring signal and the baseline signal, forming a difference signal;
performing short-time Fourier transform of the difference signal using chosen time and frequency window sizes, and time steps, forming thereby a two-dimensional array in time and frequency;
calculating the standard deviation of the short-time Fourier transform array along the time-axis for each frequency; and
summing the standard deviations as a function of frequency.

33. The method of claim 32, wherein said step of performing temperature compensation comprises:
dividing the monitoring signal into a chosen number of equal-duration time bins as a function of time;
calculating the cross-correlation function for the monitoring signal and the baseline signal for each time bin;
determining a time shift for each time bin by locating a peak of the cross correlation function for each time bin; and
assigning a value of the monitoring signal to each bin corresponding to a value of the monitoring signal at the shifted time for that bin, whereby a temperature-compensated monitoring signal is generated.

34. The method of claim 32, further comprising the steps of filtering the received vibrational signals after said step of receiving the vibrational signals generated in the wall of said metallic structure in response to the chirp signal for both of said steps of producing a baseline signal and for producing a monitoring signal.

35. The method of claim 32, wherein the chirp signals have a spectral content of between about 1 kHz and about 1 MHz.

36. The method of claim 32 wherein said elongated metallic structure comprises at least one structure chosen from a length of metallic pipe, a metallic pipe assembly, a flange, an elbow, a tee, a reducer, a weld, a vessel, a storage tank, and a storage container.

37. The method of claim 32 wherein the monitoring signal is produced subsequent to when the baseline signal is produced.

38. The method of claim 32, further including the step of comparing the change in the monitoring signal for two adjacent pipe segments, whereby the localization of changes to said metallic structure within one of the segments is determined.

* * * * *

UNITED STATES PATENT AND TRADEMARK OFFICE
CERTIFICATE OF CORRECTION

PATENT NO. : 10,473,625 B2
APPLICATION NO. : 15/751429
DATED : November 12, 2019
INVENTOR(S) : Alp T. Findikoglu It is certified that error appears in the above-identified patent and that said Letters Patent is hereby corrected as shown below:

In the Claims

In Claim 1, Column 18, Line 22, replace "at east one" with –at least one–.

In Claim 25, Column 22, Line 19, replace "setallic" with –metallic–.

In Claim 32, Column 24, Lines 14 and 15, replace "temperatures compensated" with –temperature-compensated–.

Signed and Sealed this
Fourth Day of February, 2020

Andrei Iancu
*Director of the United States Patent and Trademark Office*